United States Patent [19]
Nagano et al.

[11] 4,026,291
[45] May 31, 1977

[54] ARTICLE FOR TREATING SECRETING FLUID OF THE HUMAN BODY

[76] Inventors: Tadashi Nagano, 6-5-5, Hatanodai Shinagawa, Tokyo; Nobuakira Fujinami, 2-9-21, Shonan-Takatori Yokosuka, Kanagawa, both of Japan

[22] Filed: May 16, 1975

[21] Appl. No.: 578,068

[30] Foreign Application Priority Data

May 25, 1974 Japan .............................. 49-58922

[52] U.S. Cl. ................................. 128/284; 128/287
[51] Int. Cl.² ...................... D21D 3/00; A61F 13/16
[58] Field of Search .......... 128/284, 296, 270, 287; 260/231

[56] References Cited
UNITED STATES PATENTS

| | | | |
|---|---|---|---|
| 3,172,817 | 3/1965 | Leupold et al. | 128/284 X |
| 3,371,667 | 5/1968 | Morse | 128/296 X |
| 3,386,441 | 6/1968 | De Merre | 128/284 |
| 3,554,863 | 1/1971 | Hervey et al. | 128/284 X |
| 3,617,439 | 11/1971 | Chapman | 128/284 X |

*Primary Examiner*—Lawrence Charles
*Attorney, Agent, or Firm*—Fred Philpitt

[57] ABSTRACT

A compact article for treating fluid of the human body having an absorbent core member having the function of deodorizing, sterilizing, and coagulating the fluid and being made of a cationized cellulose fiber containing nitrogen, an inner water-proofing member for preventing the fluid from permeating to the back side of the article and being made of a cellulose fiber, and an outer cover member for covering both the inner and core members and being made of cellulose or artificial fiber or a mixture of the cellulose and artificial fibers.

1 Claim, 1 Drawing Figure

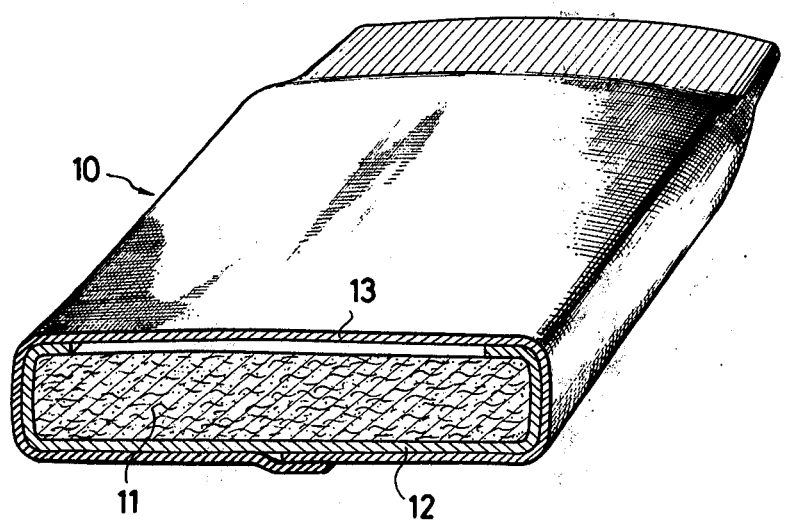

ARTICLE FOR TREATING SECRETING FLUID OF THE HUMAN BODY

FIELD OF THE INVENTION

The present invention relates to an article for treating secreting fluid of the human body which is utilized as a physical or sanitary napkin, a diaper for baby, a bedding, a bandage, and the like.

BACKGROUND OF THE INVENTION

Various improvements to articles for treating secreting fluid of the human body have heretofore been made, but none of these improvements have been sufficiently able to satisfy the requirements of the users. Consequently, an object of the present invention is to provide an article for treating secreting fluid of the human body that satisfies there requirements and the principal improvements being the use of a specific cellulose fiber.

Also, another object of the present invention is to provide an article for treating secreting fluid of the human body that can remove an odor emanated from the secreting fluid of the human body and can rapidly and effectively prevent the increase of bacteria and disease germs.

Still another object of the present invention is to provide an article for treating secreting fluid of the human body that can prevent the secreting fluid of the human body, particularly colored matter such as blood, and the like from permeating to the back side of said article by coagulating it.

A further object of the present invention is to provide an article for treating secreting fluid of the human body and can prevent said secreting fluid from permeating into the article in a spot-like manner to the back side of said article.

A still further object of the present invention is to provide an article for treating secreting fluid of the human body which is convenient since the article material to be used can be made of a smaller size as compared with the conventional similar articles thus, the whole body of the product can be made in a compact form.

BRIEF DESCRIPTION OF THE DRAWING

The single drawing shows an enlarged sectional view of the one embodiment of the present invention.

DETAILED DESCRIPTION OF THE INVENTION

As illustrated in the embodiment shown in the attached drawing, an article 10 for treating secreting fluid of the human body of the present invention comprises an absorbent core member 11 made of a cationized cellulose fiber containing nitrogen, an inner waterproofing member 12 made of a cellulose fiber, and an outer cover member 13 made of a cellulose or chemical fiber or a mixture of cellulose and chemical fibers, and covering both said core and inner members.

A cationized cellulose fiber containing nitrogen, which is the principal material to be used in the present invention, can be produced by the methods of the prior arts, for instance, this type of fiber can be produced by a method of reacting an alkaline cellulose with diethylaminoethyl chloride (U.S. Pat. Nos. 2,591,748 and 2,623,042), a method of Hofmann-degrading a carbamoyl-ethylated pulp, and the like. According to the method of the present invention, the cationized cellulose fiber containing nitrogen can be produced by using inexpensive cellulose fibers such as a standard pulp which is derived from a sulfate or sulfite process, and the like which are generally and widely used in the industry. The pulp is mixed with an alkaline aqueous solution containing an inexpensive cyanamide, alkali metal cyanamide and/or alkaline earth metal cyanamide. The aqueous suspension is prepared under a normal pressure at a proper temperature above the freezing point of the aqueous suspension. The producing method will be described as follows.

In cyanamide compounds such as sodium cyanamide, potassium cyanamide, lithium cyanamide, calcium cyanamide, barium cyanamide and strontium cyanamide, as well as alkali metal cyanamides or alkaline earth cyanamides, and lead cyanamide may be used in the present method. Besides cyanamides, salts of cyanamide contain cyanamide compounds such as $CaNCN$, $Na_2NCN$ may be perfectly substituted with metals. In order to obtain a desired reaction, it is necessary to react the cellulose fiber with an aqueous solution in which a cyanamide is mixed with an alkaline aqueous solution containing a hydroxide of an alkali metal or alkaline earth metal, and also with an aqueous solution in which an alkali metal cyanamide or alkaline earth metal cyanamide is dissolved in water. If a mixture of alkaline earth metal and cellulose fiber is not desirable, the fiber may be mixed with an aqueous solution that is prepared by dissolving an alkaline earth metal cyanamide with water. Thereafter the steps are acidifying the aqueous solution with an acid or carbonic acid gas, precipitating the alkaline earth metal, removing it to the outside of the system, and adding a hydroxide of an alkali metal thereto. Thereby adjusting the pH of the aqueous solution so as to make it above about 9, preferably above about 11, or with an aqueous solution prepared by dissolving an alkaline earth metal cyanamide with water. Thereafter adding an aqueous solution containing an alkali metal carbonate, precipitating the alkaline earth metal carbonate, and removing it. In case an alkali metal cyanamide or alkaline earth metal cyanamide is dissolved in water to prepre an aqueous solution, and an alkali metal carbonate is added to an aqueous solution of an alkaline earth cyanamide, generally, those types of aqueous solutions show an alkali property. For instance, a saturated aqueous solution of calcium cyanamide shows a range of 12 to 13 in pH. The aqueous solution after adding an alkali metal carbonate to the saturated aqueous solution and precipitating the alkaline earth metal carbonate shows approximately the same pH. Therefore the same effect can be obtained as the example where a hydroxide of an alkali metal or alkaline earth metal is added to the solution. To obtain the required pH reaction in the present method it is necessary that it be carried out in an alkaline aqueous medium whose pH is above 9, preferably above 11, depending on the desired nitrogen substitution degree.

The chemical reaction between a cyanamide and a cellulose fiber by the method of the present invention is not clearly understood. Nevertheless, in an example where a cyanamide is mixed with an alkaline aqueous solution containing a hydroxide of an alkali metal or alkaline earth metal, or in an example where an alkali metal cyanamide or alkaline earth metal cyanamide is dissolved in water to prepare an aqueous solution, generally, it has been known that hydrogen cyanamide ion (HNCH)⁻ is formed as represented by the following reaction formulae.

$$H_2NCN + NaOH \rightleftharpoons NaHNC \rightleftharpoons Na^+ + NHCN^-$$
$$2CaNCN + 2H_2O \rightleftharpoons Ca(HNCN)_2 + Ca(OH)_2$$
$$Ca(HNCN)_2 \rightleftharpoons Ca^{++} + 2HNCN^-$$
$$Na_2NCN + H_2O \rightleftharpoons NaHNCN + NaOH$$
$$NaHNCN \rightleftharpoons Na^+ + HNCN^-$$

According to tests conducted with infrared spectrometry and Raman spectrometry, cyanamides are also considered to have N-cyanoamine structure: $NH_2—C\ N$ (carbamic acid nitrile), carbodiimide structure: $NH=C=NH$ formed by tautomerism, and $H^-H—C\ N^+H$ structure. The cellulose fiber containing nitrogen according to the method of the present invention is considered to be a reaction product of said hydrogen cyanamide ion or cation and an active group in the cellulose fiber, for instance, hydroxyl group. Assuming as described above, it is necessary to have an active group for causing a reaction to produce the specific cellulose fiber. As noted previously the conventional pulp which is used in normal paper pulp industry or the other industries, can also be employed. As described above, cyanamides compounds such as cyanamides, alkali metal cyanamides and alkaline earth metal cyanamides may be used. With respect to a type of cyanamide, there is, for example, a commercially available cyanamide solution, namely, calcium cyanamide (CaNCH). Thus, the method of the present invention has the characteristic of being inexpensive and easily available. A large quantity of this cyanamide is used today as lime nitrogen fertilizers. A desired characteristic of the reaction in the method of the present invention is in that the reaction proceeds under normal pressure at any temperature above the freezing point of the suspension. Further, additional reaction requirements such as the ratio of cyanamide to the cellulose fiber, density of cyanamide dissolved in a suspension of reaction mixture, reaction time, and pH and reaction temperature, are an influence on the substitution degree of nitrogen, which is substituted in cellulose fiber, and the velocity of the substitution. For instance, the greater the ratio of whole cyanamide for cellulose fiber and also the longer the reaction time is, the higher the nitrogen substitution degree to the cellulose fiber becomes. Also, the higher the reaction temperature is, the more rapid the substitution velocity becomes.

It is to be noted that the method of the present invention can be carried out by various kinds of procedures. For example, an aqueous solution may be prepared by previously dissolving a cyanamide, alkali metal cyanamide, or alkaline earth metal cyanamide in water, and then removing unsoluble residue such as carbon, and the like by a settling method or normal solid-liquid separating method. The solution may be added to the cellulose fiber, and a cyanamide and a hydroxide of an alkali metal or alkaline earth metal may be added to a suspension in which cellulose fiber is previously suspended in water. Another example, as described in the foregoing, the cellulose fiber may be added in an aqueous solution prepared by previously dissolving an alkaline earth metal cyanamide in water, and if necessary, removing the unsoluble residue. Thereafter adding an acid or carbonic acid gas to acidify the aqueous solution, for instance, to make pH 5, and thereby forming an insoluble precipitate of an alkaline earth metal. Then, removing it by a normal solid-liquid separating method and thereafter adding newly an alkali metal hydroxide to the cyanamide aqueous solution. Thereby making again the pH of the aqueous solution above 9, preferably about 11. The preferable procedure is one in which the cellulose fiber is mixed with an aqueous solution prepared by previously dissolving an alkaline earth metal cyanamide such as calcium cyanamide in water, and if necessary, removing the unsoluble residue. Thereafter adding an alkali metal carbonate such as sodium carbonate to precipitate the insoluble carbonate of the alkaline earth metal, and removing it by normal solid-liquid separating method, and thereby an aqueous suspension is prepared. On the other hand, the cellulose fiber can be used as it is and can previously be pre-treated with a strongly alkaline aqueous solution or weakly alkaline aqueous solution, or can mechanically be pretreated. The resulting suspension of cyanamide and cellulose fiber is retained for a sufficient time at a desirable temperature in order to obtain a desired nitrogen substitution degree. The nitrogen substitution degree is, as described in the foregoing, increased with the reaction time, and generally, the nitrogen substitution degree becomes maximum after a period of 6 to 24 hours. The cellulose fiber containing nitrogen is separated from the suspension after reaction by the normal separating method, and is sufficiently rinsed, and thereafter is changed into goods of various forms. Meanwhile, the alkaline aqueous solution containing unreacted cyanamide after separating said cellulose fiber containing nitrogen is circulated and is used again.

The reaction in the method of the present invention readily proceeds, as described above, under a normal pressure at any temperature above the freezing point of the reaction suspension. The reaction operation and the reaction process can extremely be simplified, and simultaneously, the cellulose fiber containing nitrogen can economically be obtained since calcium cyanamide CaNCN, which is inexpensive and readily available as a nitrogen compound, can be used. Moreover, cellulose fiber containing nitrogen obtained by the method of the present invention can adsorb various kinds of matters that are anionized in the aqueous medium.

Also, the cation degree of cellulose fiber containing nitrogen obtained by the present invention may be represented by the nitrogen substitution degree, and such nitrogen substitution degree as considered to attain the object imposed on the article 10 for treating secreting fluid of the human body according to the present invention is in the range of 0.5 – 10%, preferably, 1– 5%.

A cottonlike web or mat or a mixture of a cottonlike web or mat produced by a dry-type preparing method after mechanically disentangling said cationized cellulose fiber containing nitrogen in a dried sheet state, a powder material produced by mechanically pulverizing said fiber in dried sheet state, and a piled body of tissue papers. This piled body is produced by a wet-type paper preparing method after beating lightly with a brush said fiber in a wet slurry state is used for the absorbent member 11 of an article 10 for treating secreting fluid of the human body of the present invention. In both cases the cottonlike web or mat, the powder material, the piled body of tissue papers, and the like is used, they are provided with many kinds of physical properties and effects that they feel extremely soft. They show bulkiness, softness, moisture absorption, liquid absorption, strongly deodorizing property, and sterilizing property based on the high cationization, and they electrically adsorb the anionic colored matters, and they have a chemically coagulating property. Also, the property of coagulating blood can be improved further by treating said cellulose fiber containing nitrogen with an astringent or gelatinizing agent. As to the types of astringents or gelatinizing agents, well known materials such as tannic acid, alum, ferric chloride, or polyethyleneoxide, carboxymethyl-cellulose, and the like can be used. In the present method, it is possible to use many kinds of methods such as a method of dipping the cationized cellulose fiber containing nitrogen into an aqueous solution of those astringents or gelatinizing agents, and dehydrating by compression, a method of mixing said cellulose fiber containing nitrogen with a powdery astringent or gelatinizing agent, and a method of mixing an astringent or gelatinizing agent with said cellulose fiber containing nitrogen. Thereafter preparing a tissue paper, and the like.

A thin sheet made of normal fiber, treated for water-repelling or water-proofing or water-resisting, or water-proofing and water-resisting, or water-repelling and water-resisting is used for the water-proofing member 12 in the present invention so as to prevent relatively transparent secreting liquid of the human body passing through the absorbent member 11 from permeating to the back side of the present article. As to the type of a material that forms the water-proofing member 12, it is effective to use the cationized cellulose fiber containing nitrogen instead of the conventional cellulose fiber.

In this industry, generally a water-repellent of a silicone system, wax sizing agent, petroleum resin sizing agent or the like is used to provide a water-proofing property to cellulose fiber.

For example, the water-proofing property may be provided by coating or spreading the water-repellent of the silicone system onto a thin sheet made of cellulose fiber, and particularly, in the case with cationized cellulose fiber containing nitrogen by adding said sizing agents to a wetting pulp slurry. Thereby, the adsorbed amount to said fiber is increased because said sizing agent grain being anionized is electrically and uniformly adsorbed, and thus the effects of water-repelling or water-resisting is improved. The said fiber is chemically retained in a neutral condition because the use of a sulfate bond is not required as a fixer. Therefore, such a type of cellulose fiber is preferable for the application to the article 10 for treating secreting fluid of the human body.

To achieve a water-resisting characteristic the cellulose fiber or cationized cellulose fiber containing nitrogen is made to react with formaldehyde, glyoxale, or an emulsion or liquid resin containing said compounds in dried or wetted state in alkaline or weakly acidic range. The reaction has heretofore been known as a method of conventional normal cellulose in which the lowering of water-swelling property and the small increase of water-resisting property are recognized by the formation of hemi-acetal in alkaline solution, and by the formation of acetal or formal in acidic solution, when a cellulose is reacted with an aldehyde. From the result of experiments by the present inventors, it has become clear that, in an example where the cationized cellulose fiber containing nitrogen is used it is improved by said method, and the said cellulose fiber is made more effectively resistant to water.

With respect to the water-proofing member 12 in the present invention, a thin sheet is desirable which is made of the conventional cellulose fiber or cellulose fiber containing nitrogen, used according to the purpose of the application, and previously treated for proper water-resisting and water-proofing by said method. The resulting cationized cellulose fiber containing nitrogen, treated for water-proofing and water-resisting temporarily repels liquid in contact with the immersing liquid from the adsorbent member 11, but said cellulose fiber gradually and reversely becomes to have a lyophilic property and becomes to have a characteristic that the adsorbed liquid is extended and widely dispersed. As a result, the absorbability is increased, and the counter permeation is prevented, and therefore the permeation of the immersing liquid to the back side of the present article can be prevented.

Cover member 13 in the present invention is made of a soft thin sheet having an excellent touch that covers and unifies the two layers, namely, they are said absorbent member 11 and said water-proofing member 12. As to the thin sheet, there is used a tissue paper produced from conventional cellulose fiber which is lightly beaten with a brush and is treated for water-resisting by the similar method as described above, or a non-weaven type produced from one kind of synthetic resin, semisynthetic resin and regenerated fiber, or a non-woven type prepared by mixing at least two kinds of those fibers. Also, as a material that forms the cover member 13, it is effective to use the cationized cellulose fiber containing nitrogen instead of said conventional cellulose fiber according to the purpose of the use. As to said synthetic fibers, it is possible to use crimped or divided vinylon, nylon and polyester fiber, and the like having fiber size and length capable of preparing a non-woven type. As to semi-synthetic fibers and regenerated fibers, it is possible to use crimped or divided acetate, viscose rayon, and the like having said properties.

The cover member 13 as described has water absorption properties and sensitive to human skin properties, and in an example where the cationized cellulose fiber containing nitrogen is used, the scatter of the fine fiber is not recognized at all by the effect of the cationic characteristic. Therefore it is provided with many excellent characteristics as an outer covering material suitable for an article for treating secreting fluid of the human body.

Also, the article 10 for treating secreting fluid of the human body that is described in conjunction with the attached rawing is illustrated in its simplest form. The said article for treating secreting fluid of the human body can be modified, if necessary, by adding other members to its basic structure, or by varying said form within the gist of the present invention.

Next there is described an example of a method of producing a cationized cellulose fiber containing nitrogen which example uses the fiber as the principle material. Further, experimental results of the functions of dispersing and coagulating the blood by the use of said fiber will be disclosed. Therefore it will be clear that a cationized cellulose fiber containing nitrogen is particularly outstanding as compared with conventional cellulose fibers.

Calcium cyanamide (100 g) was dissolved in 5 liters of water, and unsoluble residue such as carbon and the like was removed by filtration, to prepare an aqueous solution of calcium cyanamide. Thereafter, N-BKP, used as a cellulose fiber, was dipped in 17.5% aqueous solution of caustic soda and was filtered after one hour, and was rinsed with water. The N-BKP (100 g) being treated with the alkaline aqueous solution was added to said calcium cyanamide aqueous solution, and the suspension was stirred for about 10 minutes, and was reacted by keeping it for 16 hours under a normal pressure at 70° C. Then pH of the suspension was 12.5 The reaction product was separated from the suspension by filtration and was rinsed with water, to obtain a cationized N-BKP containing nitrogen.

The resulting N-BKP was dried to become sheet from, and it was mechanically disentangled in dried state, and thin sheets having each scaled amount of 42g/m², 36g/m², 39g/m² and 51 g/m² were obtained by a hand paper preparing method, and the latter two fiber thin sheets were treated with carboxy cellulose, and alum. On the other hand, a thin sheet having a scaled amount of 42 g/m² was obtained from N-BKP generally used for the conventional sanitary napkings, and the like by the hand paper preparing method. Thereafter, one drop (0.056 g) of blood was dropped with a pipet on those sheets, to disperse and coagulate the blood. Dispersion time which is the time from drop to coagulation, and dispersion area which is an area corrected from an area dispersed from the dropped point to a value in a scaled amount 30 g/m² are shown in the following table.

TABLE

| | Samples | Nitrogen substitution degree | Hand made paper scaled amount (g/m²) | Dispersion time (sec.) | Dispersion area (cm²) | Dispersion velocity (cm²/sec.) | Coagulated amount (g blood/g paper) |
|---|---|---|---|---|---|---|---|
| (1) | N-BKP containing nitrogen to be used in the present invention | 5 | 42 | 11.8 | 5.33 | 0.40 | 3.36 |
| | | 3 | 36 | 12.8 | 6.18 | 0.48 | 3.02 |
| | | 1 | 39 | 15.1 | 7.45 | 0.52 | 2.44 |
| (2) | Said (1) treated with 5%CMC | 3 | 31 | 15.9 | 5.82 | 0.37 | 3.15 |
| (3) | Said (1) treated with 12% alum | 3 | 51 | 6.2 | 4.80 | 0.78 | 3.89 |
| (4) | N-BKP to be used in conventional articles | | 42 | 16.8 | 9.75 | 0.58 | 1.92 |

We claim:
1. A compact article for treating secreting fluid of the human body comprising an absorbent core member made of a cationized cellulose fiber and containing nitrogen in an amount ranging from 0.5 to 10 percent, said fiber being a mixture of a fiber and an alkaline aqueous solution of cyanamide compounds, said core member being treated with an astringent or gelatinizing agent consisting of at least tannic acid, alum, ferric chloride, polyethylene oxide, polyacrylic acid soda and carboxymethyl cellulose;

an inner water-proofing member made of a cellulose fiber and partially covering said core member, said inner member preventing said secreting fluid from permeating to the backside of said article; and an outer cover member made of cellulose or artificial fiber or a mixture of cellulose and artificial fibers and completely covering both said core and inner members.

* * * * *